(12) United States Patent
Mennen

(10) Patent No.: US 9,447,032 B2
(45) Date of Patent: Sep. 20, 2016

(54) UREA STRIPPING PROCESS FOR THE PRODUCTION OF UREA

(75) Inventor: Johannes Henricus Mennen, Meijel (NL)

(73) Assignee: STAMICARBON B.V., Sittard (NL)

(*) Notice: Subject to any disclaimer, the term of this patent is extended or adjusted under 35 U.S.C. 154(b) by 710 days.

(21) Appl. No.: 13/504,121

(22) PCT Filed: Jan. 7, 2011

(86) PCT No.: PCT/NL2011/050012
§ 371 (c)(1),
(2), (4) Date: Aug. 10, 2012

(87) PCT Pub. No.: WO2011/084060
PCT Pub. Date: Jul. 14, 2011

(65) Prior Publication Data
US 2012/0302789 A1    Nov. 29, 2012

(30) Foreign Application Priority Data
Jan. 7, 2010  (EP) .................................... 10150235

(51) Int. Cl.
*C07C 273/04*    (2006.01)

(52) U.S. Cl.
CPC .................................. *C07C 273/04* (2013.01)

(58) Field of Classification Search
CPC .................................................... C07C 273/04
USPC ............................................................ 564/67
See application file for complete search history.

(56) References Cited

U.S. PATENT DOCUMENTS

| 4,003,928 A | 1/1977 | Heunks |
| 4,504,679 A * | 3/1985 | Inoue et al. ..................... 564/67 |
| 6,114,579 A * | 9/2000 | Van Wijck ....................... 564/67 |

FOREIGN PATENT DOCUMENTS

| EP | 0 212 744 | 3/1987 |
| EP | 1 279 663 | 1/2003 |
| GB | 2 083 471 | 9/1980 |
| WO | WO2009008422 | * 1/2009 .............. B01J 23/44 |

OTHER PUBLICATIONS

Translation of WO2009008422, published Jan. 2009.*
International Search Report for PCT/NL2011/050012, mailed Apr. 12, 2011, 2 pages.

* cited by examiner

*Primary Examiner* — Paul A Zucker
*Assistant Examiner* — Mark Luderer
(74) *Attorney, Agent, or Firm* — Morrison & Foerster LLP

(57) ABSTRACT

The invention relates to a process for producing urea wherein an aqueous urea solution, leaving a urea reaction zone is fed to a stripper, where a part of the non-converted ammonia and carbon dioxide is separated from the aqueous urea solution, which solution leaves the stripper to a first recovery section of one or more serial recovery sections and is subsequently fed to one or more urea concentration sections, wherein the urea solution leaving the stripper is subjected to an adiabatic expansion, thus creating a vapor and a liquid, which are separated before the liquid enters a first recovery section and the vapor is condensed. The invention further relates to a urea plant comprising a stripper and a first recovery section, wherein an adiabatic expansion valve and a liquid/gas separator is provided between the stripper and the first recovery section.

14 Claims, 3 Drawing Sheets

UREA STRIPPING PROCESS FOR THE PRODUCTION OF UREA

CROSS-REFERENCE TO RELATED APPLICATIONS

Figure 1:
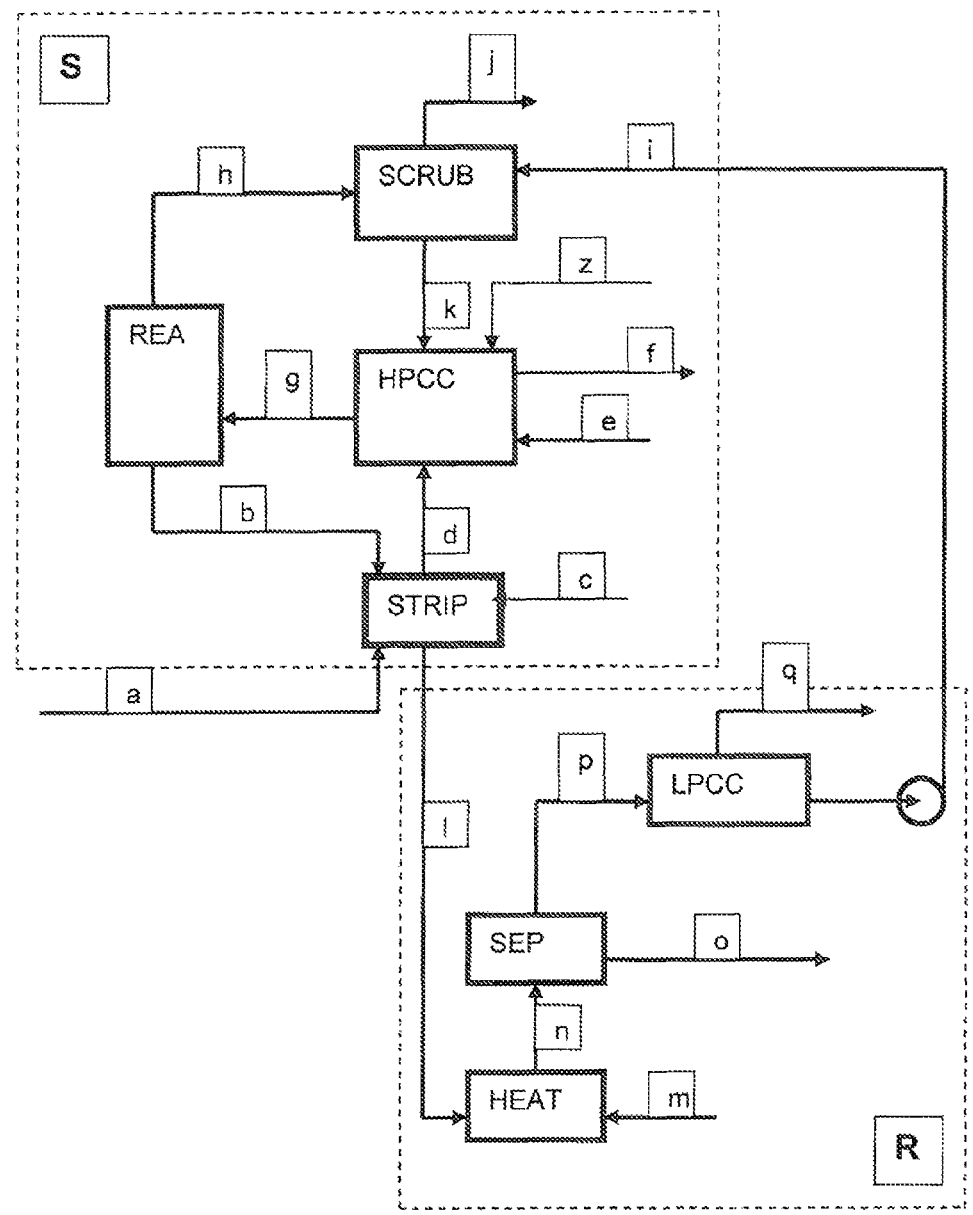

This application is the national phase of PCT application PCT/NL2011/050012 having an international filing date of Jan. 7, 2011, which claims benefit of European patent application No. 10150235.9 filed Jan. 7, 2010. The contents of the above patent applications are incorporated by reference herein in their entirety.

Urea can be prepared by introducing an ammonia excess together with carbon dioxide at a pressure between 12 and 40 MPa and at a temperature between 150 and 250° C. into a urea synthesis zone. The resulting urea formation can be presented best in the form of two consecutive reaction steps, in the first step ammonium carbamate being formed according to the exothermic reaction:

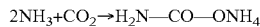

$$2NH_3 + CO_2 \rightarrow H_2N\text{—}CO\text{—}ONH_4$$

after which the ammonium carbamate formed is dehydrated in the second step to give urea according to the endothermic equilibrium reaction:

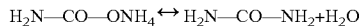

$$H_2N\text{—}CO\text{—}ONH_4 \leftrightarrow H_2N\text{—}CO\text{—}NH_2 + H_2O$$

The extent to which these reactions take place depends among other things on the temperature and the ammonia excess used. The reaction product obtained in a urea synthesis solution substantially consisting of urea, water, unbound ammonia and ammonium carbamate. The ammonium carbamate and the ammonia are removed from the solution and are generally returned to the urea synthesis zone. In addition to the above-mentioned solution in the urea synthesis zone, a gas mixture is formed which consists of unconverted ammonia and carbon dioxide together with inert gases, the so called reactor off-gas. The urea synthesis section may comprise separate zones for the formation of ammonium carbamate and urea. These zones may also be combined in a single apparatus.

In a urea stripping plant the decomposition of the ammonium carbamate that has not been converted into urea and the expulsion of the usual ammonia excess largely takes place at a pressure that is essentially almost equal to the pressure in the synthesis reactor. This decomposition and expulsion take place in one or more stripper(s) installed downstream of the reactor, possibly with the aid of a stripping gas such as, for example, carbon dioxide and/or ammonia, and with the addition of heat. It is also possible to apply thermal stripping. Thermal stripping means that use is made exclusively of the supply of heat to decompose ammonium carbamate and remove the ammonia and carbon dioxide present from the urea solution. The gas stream leaving a thermal stripper contains ammonia and carbon dioxide which are condensed in a high-pressure condenser and then returned to the urea synthesis zone.

In a urea stripping plant the synthesis zone is operated at a temperature of 160-240° C. and preferably at a temperature of 170-220° C. The pressure in the synthesis reactor is 12-21 MPa, preferably 12.5-20 MPa. The ammonia to carbon dioxide molar ratio (N/C ratio) in the urea synthesis zone of a stripping plant lies usually in between 2.2 and 5 and preferably between 2.5 and 4.5 mol/mol. The synthesis zone can be carried out in a single reactor or in a plurality of reactors arranged in parallel or series.

The energy consumption to urea stripping plants is generally determined by the steam consumption. The steam is supplied to the stripper shell in the synthesis section solely or to said stripper shell and the heater shell of the urea recovery system.

After the stripping treatment, the pressure of the stripped urea solution is reduced in the urea recovery and the urea solution is concentrated by the evaporation of water. The produced carbamate stream formed in the recovery section operated at a lower pressure than the pressure in the synthesis section is preferably returned to the urea synthesis section operating at synthesis pressure. The recovery section is generally a single section or can be a plurality of recovery sections arranged in series.

In a recovery section the non-converted ammonia and carbon dioxide in the urea solution is separated from the urea and water solution. A recovery section comprises usually a heater, a liquid/gas separation section and a condenser. The urea solution entering a recovery section is heated to vaporize the volatile components ammonia and carbon dioxide from that solution. The heating agent used in the heater is usually steam. The formed vapor in said heater is separated from the aqueous urea solution in the liquid/gas where after said vapor is condensed in the condenser. The released condensation heat is usually dissipated in cooling water.

A frequently used process for the preparation of urea according to a stripping process is the carbon dioxide stripping process as for example described in Ullmann's Encyclopedia of Industrial Chemistry, Vol. A27, 1996, pp 333-350. In this process, the synthesis section followed by one or more recovery sections. The synthesis section comprises, a reactor a stripper, a condenser and a scrubber in which the operating pressure is in between 12 and 18 MPa and preferably in between 13 and 16 MPa. In the synthesis section the urea solution leaving the urea reactor is fed to a stripper in which a large amount of non-converted ammonia and carbon dioxide is separated from the aqueous urea solution. Such a stripper can be a shell and tube heat exchanger in which the urea solution is fed to the top part at the tube side and a carbon dioxide feed to the synthesis is added to the bottom part of the stripper. At the shell side, steam is added to heat the solution. The urea solution leaves the heat exchanger at the bottom part, while the vapor phase leaves the stripper at the top part. The vapor leaving said stripper contains ammonia, carbon dioxide and a small amount of water. Said vapor is condensed in a falling film type heat exchanger or a submerged type of condenser that can be a horizontal type or a vertical type. A horizontal type submerged heat exchanger is described in Ullmann's Encyclopedia of Industrial Chemistry, Vol. A27, 1996, pp 333-350. The heat released by the exothermic carbamate condensation reaction in said condenser is usually used to produce steam that is used in a down stream urea processing section for heating and concentrating the urea solution. Since a certain liquid residence time is created in a submerged type condenser, a part of the urea reaction takes already place in said condenser. The formed solution, containing condensed ammonia, carbon dioxide, water and urea together with the non-condensed ammonia, carbon dioxide and inert vapor is sent to the reactor. In the reactor the above mentioned reaction from carbamate to urea approaches the equilibrium. The ammonia to carbon dioxide molar ratio in the urea solution leaving the reactor is generally in between 2.5 and 4 mol/mol. It is also possible that the condenser and the reactor are combined in one piece of equipment. An example of this piece of equipment as described in Ullmann's Encyclopedia of Industrial Chemistry, Vol. A27, 1996, pp 333-350. The formed urea solution leaving the urea reactor is supplied to the stripper and the inert vapor containing non-condensed ammonia and carbon dioxide is sent to a scrubbing section operating at a similar pressure as the reactor. In that scrubbing section the ammonia and carbon dioxide is scrubbed from the inert vapor. The formed carbamate solution from the down stream recovery system is used as absorbent in that scrubbing section. The urea solution leaving the stripper in this synthesis section requires a urea concentration of at least 50% by weight and preferably at least 53% by weight to be treated in one single recovery system downstream the stripper. The recovery section comprises a heater, a liquid/gas separator and a condenser. The pressure in this recovery section is between 0.2 to 0.5 MPa. In the heater of the recovery section the bulk of ammonia and carbon dioxide is separated from the urea and water phase by heating the urea solution. Usually steam is used as heating agent. The urea and water phase, contains a small amount of dissolved ammonia and carbon dioxide that leaves the recovery section and is sent to a downstream urea processing section where the urea solution is concentrated by evaporating the water from said solution. The vapor released in the heater comprises ammonia, carbon dioxide and water. Said vapor is condensed in a condenser. The heat of condensation is dissipated in cooling water. The formed carbamate is used as absorbent in said scrubber in the synthesis section. Some non-condensed vapor leaving that condenser is sent to a condenser or absorber in order to purify the inert before releasing it into the atmosphere.

A purpose of the invention is to minimize the energy consumption of a urea stripping plant. Accordingly there is provided a process for producing urea wherein an aqueous urea solution, leaving a urea reaction zone is fed to a stripper, where a part of the non-converted ammonia and carbon dioxide is separated from the aqueous urea solution, which solution leaves the stripper to a first recovery section of one or more serial recovery sections and is subsequently fed to one or more urea concentration sections, wherein the urea solution leaving the stripper is subjected to an adiabatic expansion, thus creating a vapor and a liquid, which are separated before the liquid enters a first recovery section and the vapor is condensed, and wherein the heat released from the condensation of the vapor resulting from said expansion is used for heating purposes downstream in the process.

The adiabatic expansion of said solution results preferably in a pressure drop of at least 0.5 MPa and more preferably of at least 1 MPa.

Preferably the pressure of the vapor after the adiabatic expansion is at least 0.2 MPa and preferably 0.3 MPa higher than the pressure of the liquid entering the first recovery system.

By the adiabatic expansion of said urea solution a vapor is formed containing ammonia, carbon dioxide and a small amount of water without the need of heating that solution. The vapor may be separated from the liquid phase in a liquid/gas separator. The liquid phase containing the urea solution and a relative small amount of solved ammonia and carbon dioxide is sent to a first recovery section. According to the invention, the heat released from the condensation of the vapor resulting from said expansion is used for heating purposes downstream in the process. This particularly refers to a use in one or more downstream recovery sections or for concentrating the urea solution in one or more of the urea concentration sections.

By the application of said adiabatic expansion step the necessarily high urea concentration in the urea solution leaving the stripper is not needed anymore and may be lowered to approximately 45 to 50% by weight. This can be afforded since a part of the necessarily needed heating and/or concentrating of the urea solution in the downstream processing is done by the condensation heat of the liberated ammonia and carbon dioxide released by the adiabatic expansion step.

The applicant has found that the energy consumption of a urea plant is reduced by at least 5 percent in case a one single adiabatic expansion step is applied in between the synthesis section and the first recovery section. Further the applicant has found that the application of one single expansion step in between the synthesis section and the first recovery section can be used for increasing the capacity of existing urea plants while the energy consumption per ton of produced urea is reduced by at least 5 percent. Furthermore the application of said single expansion step in existing urea plants is able to increase the plant capacity by at least 20 percent without the need of modifications of existing equipment in the downstream recovery section.

In a further advantageous aspect relating to the recovery section, the urea solution recovery initially is conducted at low pressure. A low pressure in the field of urea production means 1-10 bar, preferably 2-6 bar. Thus, the process of the invention, in this preferred embodiment, comprises the following steps:

an aqueous urea solution, leaving a urea reaction zone is fed to a stripper, where a part of the non-converted ammonia and carbon dioxide is separated from the aqueous urea solution;

the solution leaves the stripper to a first recovery section of one or more serial recovery sections and is subsequently fed to one or more urea concentration sections;

wherein the urea solution leaving the stripper is subjected to an adiabatic expansion, thus creating a vapor and a liquid, which are separated before the liquid enters a first recovery section and the vapor is condensed, and wherein the first recovery section operates at a pressure of 1-10 bar, preferably 2-6 bar. Preferably, so as to allow an optimum energy efficiency, the heat released from the condensation of the vapor resulting from said expansion is used for heating purposes in one or more downstream recovery sections or for concentrating the urea solution in one or more of the urea concentration sections, and the first recovery section operates at a pressure of 1-10 bar, preferably 2-6 bar.

The operation of the first recovery section at a pressure which is considerably lower than the pressure reached after adiabatic expansion, brings about several advantages. Thus, e.g., low-pressure steam can be used, which yields considerable advantages since the demands for the source of the steam are less stringent, the resulting process is simpler, and, all in all, cost-saving. Also, the first recovery step (first recirculation step) at the low pressure brings about the possibility to conduct the step at temperatures lower than usual, e.g. 105° C.-150° C., preferably 120° C.-140° C. This, in turn, leads to a lower energy input. Moreover, the lower temperatures suppress the extent of unwanted side-reactions (biuret formation and hydrolyses of urea).

The invention further relates to a method for increasing the capacity of an existing urea process wherein an aqueous urea solution, leaving a urea reaction zone is fed to a stripper, where a part of the non-converted ammonia and carbon dioxide is separated from the aqueous urea solution, which solution leaves the stripper to a first recovery section of one or more serial recovery sections and is subsequently fed to one or more urea concentration sections, wherein the urea solution leaving the stripper is subjected to an adiabatic expansion, thus creating a vapor and a liquid, which are separated before the liquid enters a first recovery section and the vapor is condensed. In the art, it has not been acknowledged that the combined features of subjecting the aqueous urea solution to adiabatic expansion, and separating the resulting vapor and liquid phases before the liquid enters a first recovery section, enables increasing the capacity of an existing urea plant. Preferably, the method of increasing the capacity of an existing urea plant involves the process step in which the heat released from the condensation of the vapor resulting from said expansion is used for heating purposes in one or more downstream recovery sections or for concentrating the urea solution in one or more of the urea concentration sections. In a further preferred embodiment of the method to increase the capacity of an existing urea plant, the first recovery section operates at a pressure of 1-10 bar, preferably 2-6 bar.

A further embodiment of the invention is a urea plant comprising a stripper and a first recovery section, wherein an adiabatic expansion valve and a liquid/gas separator are provided between the stripper and the first recovery section, and wherein a gas outlet of the liquid/gas separator is connected, by means of a gas transport line, to a condensator comprised in the recovery section.

Figure 2:
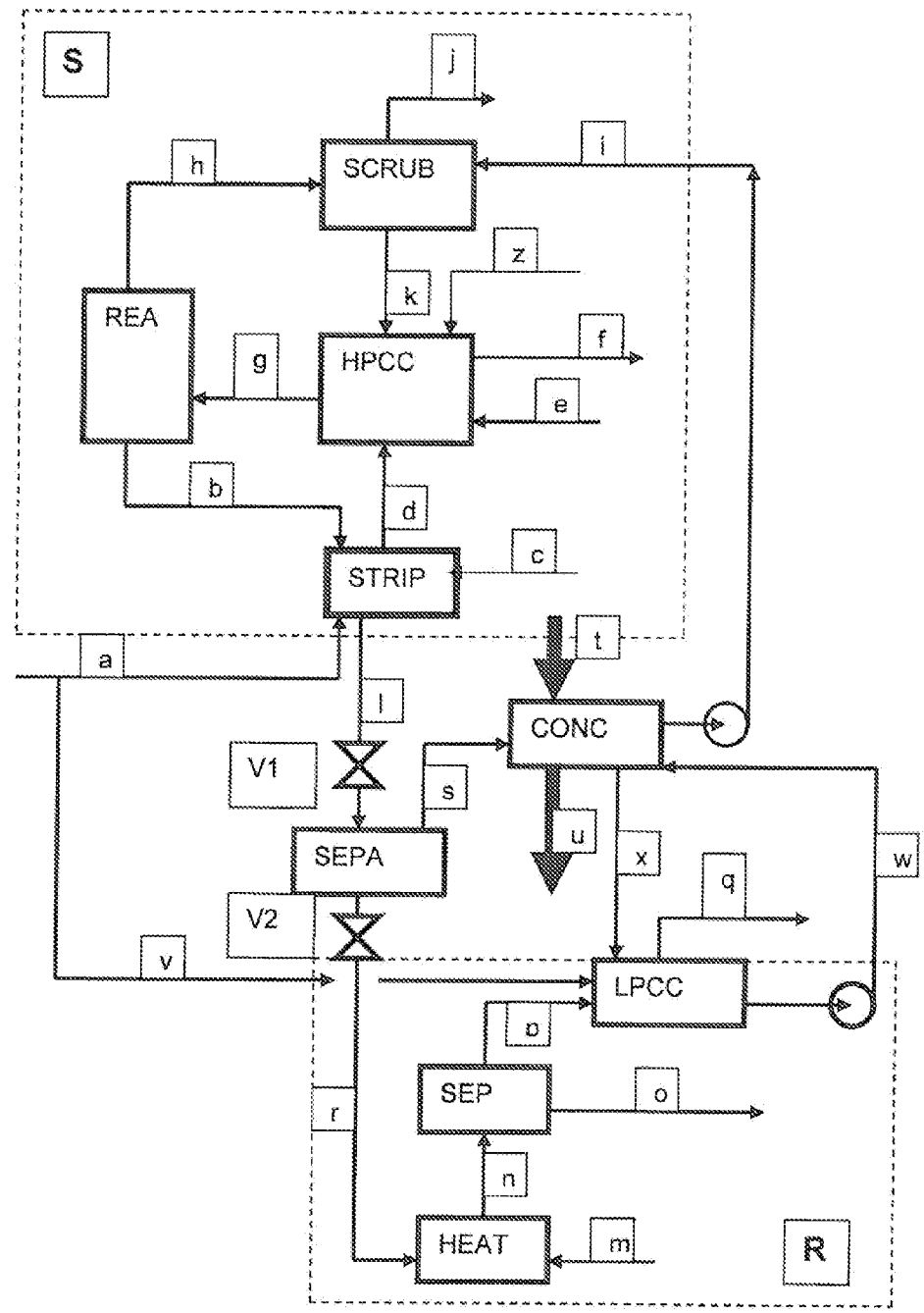
Figure 3:
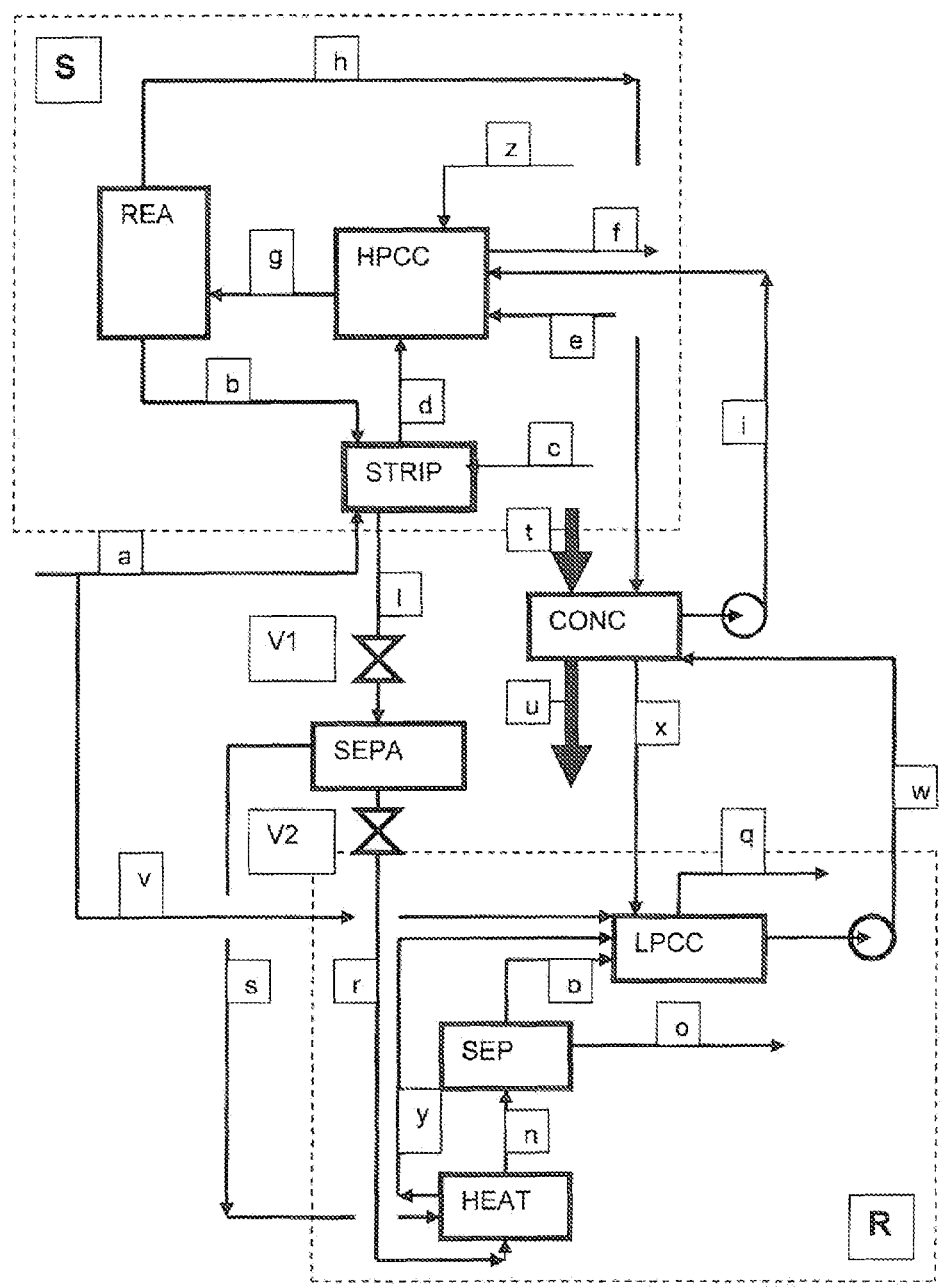

The state of the art is illustrated in FIG. 1, while two embodiments of the invention are shown in FIGS. 2 and 3.

FIG. 1 shows a typical urea stripping process as known from the prior art.

In this process, the synthesis section (S) followed by one or more recovery sections (R), after which the urea is further concentrated in one ore more downstream urea processing sections (not shown). The synthesis section comprises, a reactor (REA) a stripper (STRIP), a condenser (HPCC) and a scrubber (SCRUB) in which the operating pressure is in between 12 and 18 MPa and preferably in between 13 and 16 MPa. In the synthesis section the urea solution leaving the urea reactor (REA) is fed to a stripper (STRIP) in which a large amount of non-converted ammonia and carbon dioxide is separated from the aqueous urea solution. The stripper is a shell and tube heat exchanger in which the urea solution is fed to the top part via line (b) at the tube side and a carbon dioxide feed is added to the bottom part of the stripper via line (a) at the tube side. The carbon dioxide may but not necessarily contain inert and may comprise air for protecting the fabrication materials of the equipment and lines in the synthesis section against excessive corrosion. Urea solution from the reactor (REA) is supplied to the stripper (STRIP) via line (b) and is counter currently contacting the supplied carbon dioxide. By this the partial pressure of ammonia in the urea solution is decreased, which causes the non converted carbamate to decompose. As a heating agent, steam at a pressure of 1.5 to 2.5 MPa is supplied to the shell side of said stripper (STRIP) via line (c) in order to obtain a urea concentration in the urea solution leaving that stripper of approximately 53 to 56% by weight. The vapor leaving the stripper (STRIP) via line (d) contains ammonia, carbon dioxide and a small amount of water and is supplied to a condenser (HPCC). Ammonia is supplied to that condenser (HPCC) as well via line (e). In this condenser the ammonia and carbon dioxide is condensed into a carbamate solution. The released condensation heat is used to heat condensate that enters via line (z) to steam that exits via line (f) that is used for heating purposes in the downstream urea processing sections. As the condenser (HPCC) is a submerged type, residence time of the liquid phase is created, which causes the endothermic urea reaction to proceed. The thus formed solution together with non condensed inert vapor leaving the condenser (HPCC) is sent to the reactor (REA) via line (g) where the endothermic urea reaction approaches the equilibrium. In the top of the reactor (REA) the solution is separated from the non-condensed inert vapor. The solution is sent to said stripper (STRIP) via line (b) and the non-condensed inert vapor is sent to the scrubber (SCRUB) via line (h). In the scrubber (SCRUB) the non-condensed ammonia and carbon dioxide is separated from the inert vapor by feeding the carbamate, formed in the recovery section as absorbent via line (i). The inert vapor via line (j) is sent into the atmosphere directly or can be treated in an absorber before releasing it into the atmosphere. The formed carbamate solution in the scrubber (SCRUB) is returned to the condenser (HPCC) via line (k)

The urea solution leaving the urea stripper (STRIP) via line (l) is expanded and sent directly to a heater (HEAT) in the recovery section. The operating pressure in the recovery section is 0.2 to 0.6 MPa. To the shell side of that heater (HEAT) steam via line (m) is supplied to heat the solution to a temperature of 120-145° C. and preferably to a temperature of 130 to 140° C. The formed vapor and urea solution is sent from heater (HEAT) to separator (SEP) via line (n). In the separator (SEP) the vapor is separated from the urea solution. The urea solution leaves the heater (HEAT) in the recovery system via line (o) to a downstream urea processing section where that solution is concentrated by evaporating the water from the urea. The formed vapor from the heater (HEAT) via line (p) is sent to a condenser (LPCC). In that condenser, ammonia and carbon dioxide is condensed to form carbamate. The released condensation heat by that carbamate condensation reaction is dissipated into cooling water. The formed carbamate in that condenser (LPCC) is elevated via line (i) to the scrubber (SCRUB) in the synthesis section by means of a pump. The non-condensed vapor leaving the condenser (LPCC) via line (q) is furthermore treated in a downstream section in order to purify the inert before releasing it into the atmosphere.

The energy input to the urea plant happens by the addition of steam via line (c) at a pressure of about 2 MPa to the shell side of the stripper (STRIP). The amount of steam to heat the solution to obtain a urea concentration of at least 53% by weight amounts to 850 to 900 kg per ton of produced urea final product.

FIG. 2 shows an example of a process for producing urea according to the invention In this process, the synthesis section (S) followed by one or more recovery sections (R), after which the urea is further concentrated in one ore more downstream urea processing sections (not shown). The synthesis section comprises, a reactor (REA) a stripper (STRIP), a condenser (HPCC) and a scrubber (SCRUB) in which the operating pressure is in between 12 and 18 MPa and preferably in between 13 and 16 MPa. In the synthesis section the urea solution leaving the urea reactor (REA) is fed to a stripper (STRIP) in which a large amount of non-converted ammonia and carbon dioxide is separated from the aqueous urea solution. The stripper is a shell and tube heat exchanger in which the urea solution is fed to the top part via line (b) at the tube side and a carbon dioxide feed is added to the bottom part of the stripper via line (a). The carbon dioxide may contain inert and may comprise air for protecting the fabrication materials of the equipment and lines in the synthesis section against excessive corrosion. Urea solution from the reactor (REA) is supplied to the stripper (STRIP) via line (b) and is counter currently contacting the supplied carbon dioxide. By this the partial pressure of ammonia in the urea solution is decreased, which causes the non converted carbamate to decompose. As a heating agent, steam at a pressure of 1.5 to 2.5 MPa is supplied to the shell side of said stripper (STRIP) via line (c) in order to obtain a urea concentration in the urea solution leaving that stripper of approximately 45 to 50% by weight. The vapor leaving the stripper (STRIP) via line (d) contains ammonia, carbon dioxide and a small amount of water and is supplied to a condenser (HPCC). Ammonia is supplied to that condenser (HPCC) as well via line (e). In this condenser the ammonia and carbon dioxide is condensed into a carbamate solution. The released condensation heat is used to heat condensate that enters via line (z) to steam that exits via line (f) that is used for heating purposes in the downstream urea processing sections. As the condenser (HPCC) is a submerged type, residence time of the liquid phase is created, which causes the endothermic urea reaction to proceed. The thus formed solution together with non condensed inert vapor leaving the condenser (HPCC) is sent to the reactor (REA) via line (g) where the endothermic urea reaction approaches the equilibrium. In the top of the reactor (REA) the solution is separated from the non-condensed inert vapor. The solution is sent to said stripper (STRIP) via line (b) and the non-condensed inert vapor is sent to the scrubber (SCRUB) via line (h). In the scrubber (SCRUB) the non-condensed ammonia and carbon dioxide is separated from the inert vapor by feeding the carbamate, formed in the recovery section as absorbent via line (i). The inert vapor via line (j) is sent into the atmosphere directly or can be treated in an absorber before releasing it into the atmosphere. The formed carbamate solution in the scrubber (SCRUB) is returned to the condenser (HPCC) via line (k)

The urea solution leaving the urea stripper (STRIP) via line (l) has a urea concentration of about 45 to 50% by weight and is subjected to an adiabatic expansion in valve ($V_1$) to a pressure of about 2.5 MPa. By that expansion, ammonia and carbon dioxide are liberated. The liberated ammonia and carbon dioxide in the vapor phase are separated from the urea solution in a separator (SEPA). The urea solution leaves the separator (SEPA) via line (r) and has a concentration of 50 to 55% by weight and a ammonia to carbon dioxide molar ratio of 2.8 to 3.4 mol/mol and is added via valve (V2) to the recovery system operating at a pressure of about 0.4 MPa. The liberated ammonia and carbon dioxide leaving the separator (SEPA) via line (s) is added to the shell side of a urea concentrator (CONC) that operates at a similar pressure than the pressure after the adiabatic expansion. At the tube side of that urea concentrator (CONC) urea solution is added via line (t) and is concentrated. That concentration of the urea solution takes place at sub-atmospheric pressure. The urea concentrator (CONC) can be a vertical one pass type of concentrator as well as a falling film type concentrator. By the released condensation heat at the shell side, water in the urea solution at the tube side of said concentrator (CONC) is evaporated and thus the urea solution is concentrated and leaves the concentrator via line (u). About 10% to 99% of the liberated ammonia and carbon dioxide by the adiabatic expansion and preferably 30% to 95% is condensed at the shell side of that concentrator (CONC). The urea concentration in the urea solution added to the tube side via line (t) of that concentrator is 50 to 72% by weight and preferably 60 to 70% by weight. The urea concentration in the solution leaving that concentrator (CONC) via line (u) is 72 to 96% by weight and preferably 75 to 93% by weight.

In the recovery system downstream the adiabatic expansion, the urea solution is added to a heater (HEAT) via line (r) where the urea solution is heated to 130 to 140° C. By that heating of the solution, ammonia and carbon dioxide are liberated from the solution. The urea concentration in the solution leaving the heater (HEAT) via line (o) to the one or more downstream urea processing sections is about 60 to 65% by weight. The liberated ammonia and carbon dioxide is separated from the solution in a liquid/gas separator (SEP) where after the vapor, via line (p) is transferred to a condenser (LPCC), where the vapor is condensed. To this recovery system and preferably to the condenser (LPCC) a small portion of carbon dioxide is added via line (v) in order to control the ammonia to carbon dioxide molar ratio in the formed condensed carbamate. The ammonia to carbon dioxide molar ratio in that formed carbamate in line (w) is 1.9 to 4 mol/mol and preferably 2.1 to 3.5 mol/mol. That formed carbamate is elevated to the shell side of said concentrator (CONC) where after the formed carbamate in the shell side of that concentrator is pumped to the scrubber (SCRUB) in the synthesis section via line (i). The amount of water in this carbamate stream is 19 to 40% by weight and preferably 20 to 35% by weight. To control the amount of water in the formed carbamate, water is added to either the condenser (LPCC) in the recovery section or to the shell side of the concentrator (CONC). The non-condensed vapor at the shell side of the concentrator (CONC) via line (x) is purged to the condenser (LPCC) in the recovery system where the remaining ammonia and carbon dioxide are condensed against cooling water. The inert vapor containing small amounts of ammonia and carbon dioxide leaving the condenser (LPCC) via line (q) is further treated in the downstream processing of the plant before releasing into the atmosphere.

The energy input to the urea plant via the stripper (STRIP) via line (c) in the synthesis is lowered by this invention to 750 to 830 kg per ton of produced urea product.

FIG. 3 shows an example of another embodiment of a process for producing urea according to the invention.

In this process, the synthesis section (S) followed by one or more recovery sections (R), after which the urea is further concentrated in one ore more downstream urea processing sections (not shown). The synthesis section comprises, a reactor (REA) a stripper (STRIP), a condenser (HPCC) and a scrubber (SCRUB) in which the operating pressure is in between 12 and 18 MPa and preferably in between 13 and 16 MPa. In the synthesis section the urea solution leaving the urea reactor (REA) is fed to a stripper (STRIP) in which a large amount of non-converted ammonia and carbon dioxide is separated from the aqueous urea solution. The a stripper is a shell and tube heat exchanger in which the urea solution is fed to the top part via line (b) at the tube side and a carbon dioxide feed is added to the bottom part of the stripper via line (a). The carbon dioxide may contain inert and may comprise air for protection the fabrication materials of the equipment and lines in the synthesis section against excessive corrosion. Urea solution from the reactor (REA) is supplied to the stripper (STRIP) via line (b) and is counter currently contacting the supplied carbon dioxide. By this the partial pressure of ammonia in the urea solution is decreased and causes the non converted carbamate to decompose. As a heating agent, steam at a pressure of 1.5 to 2.5 MPa is supplied to the shell side of said stripper (STRIP) via line (c). The vapor leaving the stripper (STRIP) via line (d) contains ammonia, carbon dioxide and a small amount of water and is supplied to a condenser (HPCC). Ammonia is supplied to that condenser (HPCC) as well via line (e). In this condenser the ammonia and carbon dioxide is condensed into a carbamate solution. The released condensation heat is used to produce steam via line (f) that is used for heating purposes in the downstream processing of the urea plant. As the condenser (HPCC) is a submerged type, residence time of the liquid phase is created, which causes the endothermic urea reaction to proceed. The thus formed solution together with non condensed inert vapor leaving the condenser (HPCC) is sent via line (g) to the reactor (REA) where the endothermic urea reaction approaches the equilibrium. In the top of the reactor (REA) the solution is separated from the non-condensed inert vapor. The solution is sent to said stripper (STRIP) via line (b).

The urea solution leaving the urea stripper (STRIP) via line (l) has a urea concentration of about 45 to 50% by weight and is subjected to adiabatic expansion in valve (V1) to a pressure of about 2.5 MPa. By the expansion, ammonia and carbon dioxide is liberated. The liberated ammonia and carbon dioxide in the vapor phase are separated from the urea solution in a separator (SEPA). The urea solution leaves the separator (SEPA) via line (r) and has a concentration of 50 to 55% by weight and an ammonia to carbon dioxide molar ratio of 2.8 to 3.4 mol/mol and is added via valve (V2) to the recovery system operating at a pressure of about 0.4 MPa.

The decomposed ammonia and carbon dioxide leaving the separator (SEPA) via line (s) is added to the shell side of the heater (HEAT) in the recovery system where this vapor is condensed. The released condensation heat by the carbamate condensation is used to heat the urea solution that is added to that heater (HEAT) at the tube side via line (r). About 10 to 90% of the liberated ammonia and carbon dioxide liberated by the adiabatic expansion is condensed at the shell side of the heater (HEAT). Preferably 30 to 85% of that vapor is condensed at the shell side of heater (HEAT). The formed carbamate solution together with non-condensed ammonia and carbon dioxide leave the shell side of heater (HEAT) via line (y) and is sent to the condenser in the recovery system (LPCC).

The inert vapor that leaves the reactor (REA) in the urea synthesis section via line (h) is added to the shell side of a urea concentrator (CONC) that operates at a similar pressure than the pressure after the adiabatic expansion. At the tube side of that urea concentrator (CONC) urea solution is concentrated. Concentrating the urea solution happens at sub-atmospheric pressure. This urea concentrator (CONC) can be a vertical one pass type of concentrator as well as a falling film type concentrator. By the released condensation heat at the shell side, water in the urea solution at the tube side of said concentrator is evaporated and thus the urea solution is concentrated. The urea concentration in the urea solution added to the tube side of that concentrator via line (t) is 50 to 72% by weight and preferably 60 to 70% by weight. The urea concentration in the solution leaving that concentrator (CONC) via line (u) is 72 to 90% by weight and preferably 74 to 85% by weight.

In the recovery system, downstream the adiabatic expansion, the urea solution is added to the tube side of a heater (HEAT) via line (r). The urea concentration in the solution leaving that heater (HEAT) via line (n) becomes 60 to 65% by weight. The liberated ammonia and carbon dioxide is separated from the solution in the gas/liquid separator (SEP) where after the vapor via line (p) is condensed in a condenser (LPCC). To this recovery system and preferably to the condenser (LPCC) a small portion of carbon dioxide is added via line (v) in order to control the ammonia to carbon dioxide molar ratio in the formed condensed carbamate. The ammonia to carbon dioxide molar ratio in that formed carbamate is 1.9 to 4 mol/mol and preferably 2.1 to 3.5 mol/mol. That formed carbamate is elevated via line (w) to the shell side of said concentrator (CONC) where after the formed carbamate in the shell side of that concentrator is pumped via line (i) to the condenser (HPCC) in the synthesis section. The water concentration in this carbamate is 19 to 40% by weight and preferably 20 to 35% by weight. To control that water content in the formed carbamate, water is added to either the condenser (LPCC) in the recovery section or to the shell side of the concentrator (CONC). The non-condensed vapor at the shell side of the concentrator (CONC) is purged via line (x) to the condenser (LPCC) in the recovery system where the left ammonia and carbon dioxide is condensed against cooling water. The inert vapor containing small amounts of ammonia and carbon dioxide leaving the condenser (LPCC) via line (q) is further treated in the downstream processing of the plant before releasing into the atmosphere.

The energy input to the urea plant via the stripper (STRIP) in the synthesis via line (c) is decreased by this invention to 740 to 820 kg per ton of produced urea product.

The invention claimed is:

1. A process for producing urea by converting ammonia and carbon dioxide to urea wherein an aqueous urea solution containing non converted ammonia and carbon dioxide, leaving a urea reaction zone is fed to a stripper, wherein in said stripper part of the non-converted ammonia and carbon dioxide is separated from the aqueous urea solution, which urea solution leaves the stripper to a first recovery section of one or more serial recovery sections and is subsequently fed to one or more urea concentration sections, wherein the urea solution leaving the stripper is subjected to an adiabatic expansion, thus creating a vapor and a liquid, which are separated before the liquid enters a first recovery section and the vapor is condensed, and wherein the heat released from the condensation of the vapor resulting from said expansion is used for heating downstream in the process, wherein the first recovery section is operated at a pressure of 0.1-1 MPa; and/or wherein the pressure of the vapor after the adiabatic expansion is at least 0.2 MPa higher than the pressure in the first recovery system.

2. A process according to claim 1, wherein the first recovery section is operated at a pressure of 0.1-1 MPa.

3. A process according to claim 1, wherein the adiabatic expansion results in a pressure drop of at least 0.5 MPa.

4. A process according to claim 1, wherein the pressure of the vapor after the adiabatic expansion is at least 0.2 MPa higher than the pressure in the first recovery system.

5. A process according to claim 1, wherein the heat released during condensation of the vapor is used for concentrating a urea solution in one or more of the urea concentration sections.

6. A process according to claim 1, wherein the released condensation heat of the formed vapor by the adiabatic expansion step is used for heating the urea solution in one or more downstream urea recovery sections.

7. A process according to claim 1, wherein the heating downstream in the process is selected from the group consisting of heating in one downstream recovery section, heating in a plurality of downstream recovery sections, for concentrating the urea solution in one of the urea concentration sections, for concentrating the urea solution in a plurality of urea concentration sections, and combinations thereof.

8. An improved method for preparing urea by increasing the capacity of an existing urea process wherein said process comprises converting ammonia and carbon dioxide to urea wherein an aqueous urea solution containing non converted ammonia and carbon dioxide, leaving a urea reaction zone is fed to a stripper, wherein in said stripper part of the non-converted ammonia and carbon dioxide is separated from the aqueous urea solution, which urea solution leaves the stripper to a first recovery section of one or more serial recovery sections and is subsequently fed to one or more urea concentration sections, and wherein the improvement comprises subjecting the urea solution leaving the stripper to an adiabatic expansion, thus creating a vapor and a liquid, which are separated before the liquid enters a first recovery section and the vapor is condensed, whereby heat is released; and wherein the first recovery section is operated at a pressure of 0.1-1 MPa.

9. A method according to claim 8, wherein the heat released from the condensation of the vapor resulting from said expansion is used for heating downstream in the process.

10. A urea plant comprising a stripper and a recovery section, which recovery section comprises a condensor, wherein an adiabatic expansion valve and a liquid/gas separator are provided between the stripper and the recovery section, and wherein a gas outlet of the liquid/gas separator is connected, by means of a gas transport line, to the condensor comprised in the recovery section.

11. The process of claim 2 wherein the first recovery section is operated at a pressure of 0.2-0.6 Pa.

12. The process of claim 3 wherein the adiabatic expansion results in a pressure drop of at least 1 MPa.

13. The process of claim 4 wherein the pressure of the vapor after the adiabatic expansion is at least 0.3 MPa higher than the pressure in the first recovery system.

14. The method of claim 8 wherein the first recovery section is operated at a pressure of 0.2-0.6 Pa.

\* \* \* \* \*